(12) United States Patent
Lappalainen et al.

(10) Patent No.: US 6,526,119 B1
(45) Date of Patent: Feb. 25, 2003

(54) METHOD AND ARRANGEMENT FOR DETERMINING THE MOISTURE CONTENT OF WOOD CHIPS

(75) Inventors: Timo Lappalainen, Jyväskylä (FI); Veli-Juhani Aho, Jyväskylä (FI); Markku Tiitta, Kuopio (FI)

(73) Assignee: Valtion Teknillinen Tutkimuskeskus, Espoo (FI)

(*) Notice: Subject to any disclaimer, the term of this patent is extended or adjusted under 35 U.S.C. 154(b) by 0 days.

(21) Appl. No.: 09/890,023
(22) PCT Filed: Jan. 27, 2000
(86) PCT No.: PCT/FI00/00055
§ 371 (c)(1), (2), (4) Date: Jul. 23, 2001
(87) PCT Pub. No.: WO00/45157
PCT Pub. Date: Aug. 3, 2000

(30) Foreign Application Priority Data

Jan. 28, 1999 (FI) .................................. 990153

(51) Int. Cl.[7] ........................ G01N 23/06; G01N 23/12; G01N 29/00; G01N 33/46
(52) U.S. Cl. ............................. 378/53; 378/83; 378/88
(58) Field of Search .......................... 378/51, 52, 53, 378/83, 88, 86

(56) References Cited

U.S. PATENT DOCUMENTS

| | | | |
|---|---|---|---|
| 3,944,833 A | 3/1976 | Hounsfield | 378/19 |
| 4,566,114 A | 1/1986 | Watt et al. | 378/88 |
| 5,062,299 A * | 11/1991 | Davis et al. | 73/609 |
| 5,195,116 A | 3/1993 | LeFloc'h et al. | 378/86 |
| 6,221,019 B1 * | 4/2001 | Kantorovich | 600/449 |

FOREIGN PATENT DOCUMENTS

| | | |
|---|---|---|
| EP | 0633466 | 1/1995 |
| GB | 2119733 | 11/1983 |
| SE | 382503 | 2/1976 |
| WO | 9535491 | 12/1995 |

* cited by examiner

Primary Examiner—Drew A. Dunn
(74) Attorney, Agent, or Firm—Fildes & Outland, P.C.

(57) ABSTRACT

A method and arrangement for measuring the moisture content of a flow of wood chips, through which collimated gamma radiation is directed attenuation of which in the flow of wood chips is measured. The flow of wood chips is shaped by transporting it on a trough-shaped conveyor in such a way that the length of a ray can be determined. The moisture content can be calculated on the basis of the proportion of gamma radiation passing through the flow of wood chips and the flow's thickness, as well as on the basis of the previously determined air content of the flow of wood chips.

10 Claims, 1 Drawing Sheet

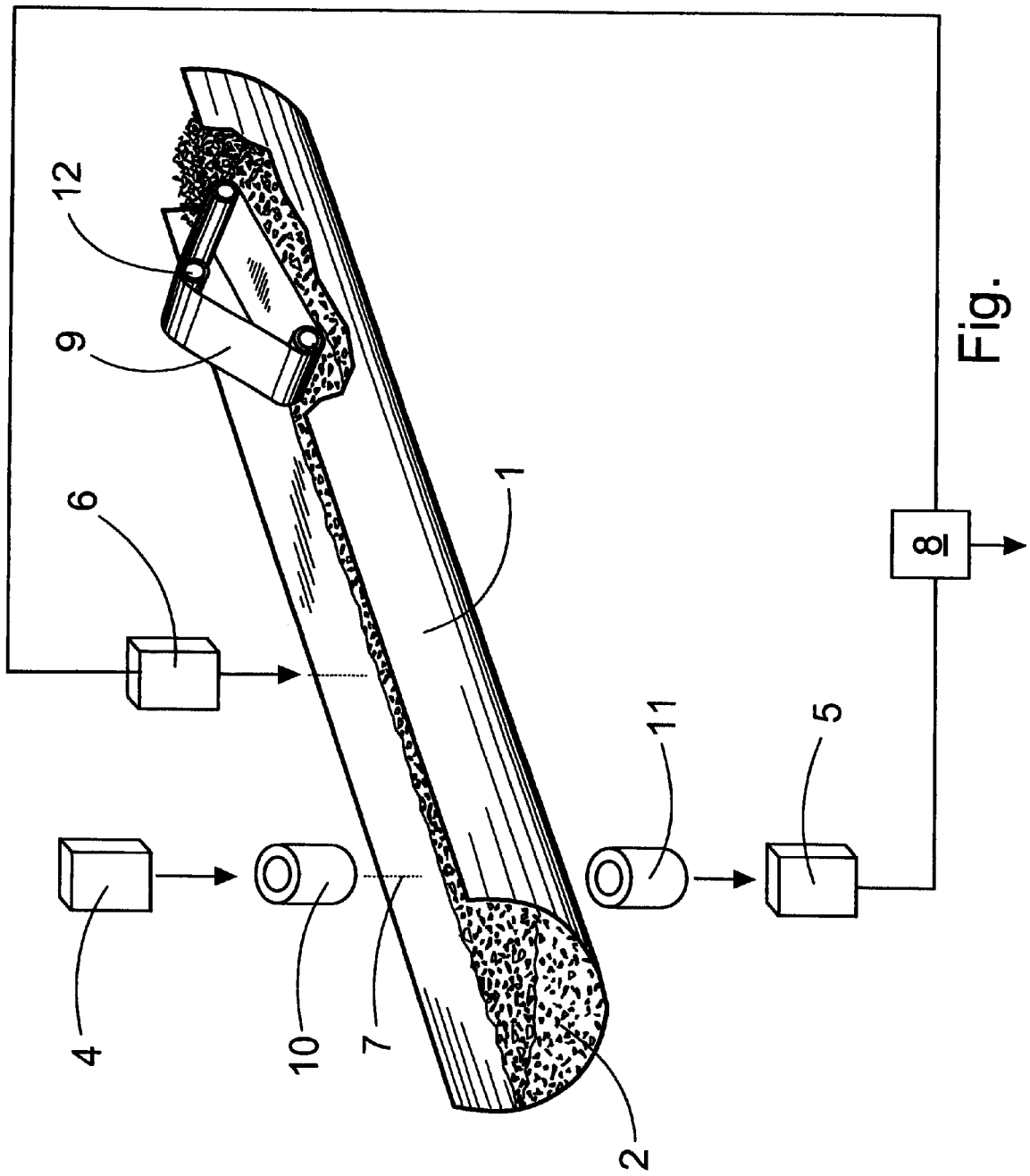

METHOD AND ARRANGEMENT FOR DETERMINING THE MOISTURE CONTENT OF WOOD CHIPS

TECHNICAL FIELD

The present invention relates to a method for determining the moisture content of wood chips, by forming an essentially homogenous flow of wood chips, by sending gamma radiation mainly transversely through the flow of chips, measuring the attenuation of the gamma radiation that has passed through the flow of chips, and determining the relative value of the total mass at the point where the gamma radiation passes through it, after which the moisture content can be obtained as functions of this value and the measured attenuation.

This invention also relates to an arrangement for measuring the moisture content of wood chips, in which there is a wood-chip conveyor with raised sides, on opposite sides of which are a gamma radiation source and a corresponding detector, i.e. a receiver.

BACKGROUND OF THE INVENTION

When cooking pulp, it is necessary to know the average moisture content of the wood chips. If the amount of timber solids and the amount of water in the wood are known, the dosing of the cooking chemicals can be optimized, in relation to the timber solids. Information on the moisture content of wood chips is important not only when making mechanical and chemical pulp, but also for wood-chip-fired heating plants, as the thermal value of wood depends very strongly on its moisture content.

Each chemical element has a specific mass attenuation constant. Thus, the composition of elements in a material or a chemical compound also determines their mass attenuation constant. It has been observed from the composition of elements in wood and water, that the mass attenuation of water is only slightly greater than that of wood. However, the density of water is, on average, twice that of wood, so that the linear attenuation constant of water is considerably greater than that of wood.

Thus, it is in principle possible to use gamma radiation to measure the moisture content of a wood material. Due to the variations in the density of wood material, its linear attenuation constant also varies considerably, preventing the accurate measurement of the moisture content of wood by measuring the attenuation of gamma radiation in wood in a single stage. However, a two-stage procedure can be used to accurately measure the moisture content and density distributions of wood in all conditions, but this requires measuring the transmission of gamma radiation in the wood material, both when it is moist and oven-dry. For obvious reasons, this type of two-stage procedure is not, however, suitable for the on-line measurement of the moisture content of wood material. The density variations in the wood material can, however, be minimized by using a chipper to cut the wood material into small pieces, so that the wood chips from different logs and the different parts of logs form a flow of wood chips, in which the individual chips are randomly mixed to form a homogenous flow, without significant mutual variations in moisture content and density.

A previously known procedure for determining the relative proportions of different components in a flow of material is by measuring the attenuation of electromagnetic radiation in a flow of material. Thus, a method is known from Finnish patent application 894786 for determining the relative proportions of material components in a flow of material, by simultaneously directing x-ray radiation and gamma radiation from separate sources and from the same point, through the flow of material. The proportions of the material components in the flow of material are calculated on the basis of the amount of x-ray radiation passing through the flow, taking into account the amount of material passed through by the x-ray radiation, which in turn is calculated on the basis of the intensity of the gamma radiation passing through the flow of material.

In addition, Finnish patent 55729 discloses a measuring device for determining the moisture content of loose material being transported on a conveyor, in which the loose material being transported on the conveyor is radiated with fast neutrons and gamma radiation, and in which on the opposite side of the conveyor there are detectors for slow neutrons and correspondingly for that proportion of the gamma radiation that passes through the loose material. The moisture content of the loose material can be calculated on the basis of the signals given by both detectors.

A drawback with these previously known methods and measuring devices is that they require, besides the source of gamma radiation and its detector, another source of radiation and a detector. This makes the devices expensive, in addition to which the methods are twice as liable to faults as those in which only a single source of radiation and a detector is required. In addition, ionizing radiation has a large environmental impact.

SUMMARY OF THE INVENTION

The present invention is intended to create a method and arrangement of the type referred to in the preface, which eliminate the drawbacks of the state of the art referred to above.

A method for measuring the moisture content of wood chips includes forming an essentially homogenous flow of wood chips, directing gamma radiation essentially transversely through the flow of wood chips, measuring the attenuation of the gamma radiation passing through the flow of wood chips, and determining the proportional value of the total mass at the penetration point of the gamma radiation, in which case, the moisture content is obtained as a function of this value and the measured attenuation. The gamma radiation is collimated from at least one side of the flow of wood chips to create a measurement ray. The length of this measurement ray in the flow of wood chips is measured, and the air content of the flow of wood chips is determined, in which case the proportional value of the mass is determined with the aid of the length and air content.

The flow of wood chips is shaped by transporting it on a conveyor with a trough-shaped cross-section, the gamma radiation being directed essentially vertically through the flow of wood chips and the conveyor. The surface level of the flow of wood chips is measured on the trough-shaped conveyor at a point, which is preferably essentially on the same straight line in the direction of travel of the wood chips as the gamma radiation. The surface level of the flow of wood chips on the trough-shaped conveyor is measured using ultrasound.

The wood chips are fed onto the conveyor with a trough-shaped cross-section up to its edges and the part that is higher than the edges may be levelled to the height of the edges by removing the excess over the edges. The gamma radiation is directed essentially vertically through the levelled flow of wood chips and the conveyor.

The air content of the wood chips is measured at regular intervals and the measurement result obtained is used to correct the moisture content of the wood chips calculated on the basis of the continuous measurement results. The flow of wood chips may be compressed before the gamma radiation, to stabilize the air content.

An arrangement to measure the moisture content of wood chips, includes a wood-chip conveyor with raised sides forming a flow of wood chips and on opposite sides of it a source of gamma radiation and a corresponding detector arranged to essentially overlap. At least one collimator for forming a collimated measurement ray and an ultrasound device above the wood-chip conveyor measure the surface level of the wood chips transported on the conveyor. A device is provided for measuring the moisture content of the wood chips transported on the conveyor on the basis of the measurement signals provided by the detector and the ultrasound device and the predetermined amount of air in the flow.

Preferably the wood-chip conveyor has a trough-shaped cross-section. A compression device above the wood-chip conveyor seen in its direction of travel before the source of collimated gamma radiation and the ultrasound device compresses the wood chips transported by the conveyor, to stabilize their air content. The compression device may be a roller, endless belt, or similar device.

According to the present invention, the moisture content can be reliably measured from a homogenous flow of material, if the latter is shaped in such a way that it has a known, or at least easily measured thickness in the direction in which it is gamma-radiated. In this case, the moisture content of the wood chips can be calculated on the basis of the proportion of gamma radiation passing through the flow of wood chips and the thickness of the flow of wood chips in the direction of the radiation. No x-ray or neutron radiation is required and the measurement can be carried out on-line in a single stage from a wood chip line. The environmental impact of the collimated, i.e. directed, radiation is small. As a result of the collimations, radiation scattering is not observed.

The linear attenuation constant of moist wood material is composed, on the one hand of the water contained in the wood, and, on the other, of the linear attenuation constant of the wood material. In this case, the moisture content of the wood material cannot be reliably determined using single-stage gamma radiation, as the attenuation of the radiation in the wood material depends not only on the moisture content, but also on the density of the wood, which can vary greatly with the measurement location. However, when wood chips are made from logs, the logs splinter into very small pieces, which are effectively mixed during chipping and screening, distributing them evenly in the wood-chip flow transported on the conveyor, so that the average density of the wood material of the wood chips is a constant in the flow of wood chips. Thus, the linear attenuation constant of the moist wood measured using the collimated gamma radiation is only affected by the amount of water appearing in the flow of wood chips (the moisture content of the wood chips), the density of the flow of wood chips, (the amount of air in it), and the thickness of the flow of wood chips in the direction of the gamma radiation. The density of the flow of wood chips in a specific conveyor system is, however, nearly constant in practice, but may vary slightly with the season of the year. Thus, the moisture content of the flow of wood chips can be reliably determined, by using gamma radiation to measure the linear attenuation constant of the flow of wood chips, if the thickness of the flow of wood chips is known at the location, and in the direction of the measurement.

Thus, the linear attenuation constant of the flow of wood chips is measured with the aid of the attenuation of collimated gamma radiation taking place in the flow of chips, and, if the thickness of the flow of chips does not remain constant but varies, its thickness can be measured using some surface level meter that is, as such, known. In this way, the method permits the on-line measurement of the moisture content of wood chips. The measurement method does not depend on the form of the water, as the absorption cross-sections are specific constants for each atom, irrespective of the physical or chemical form of substance. The method is based on the measurement of the transmission of the gamma radiation, allowing it to be used to measure the average moisture content of the flow of wood chips.

In one preferred embodiment of the invention, the flow of wood chips is shaped by transporting it on a conveyor with a trough-shaped cross-section and directing the gamma radiation at essentially right-angles through the flow of wood chips and the conveyor. When using a trough-shaped conveyor, the level of the surface of the layer of wood chips is measured in a manner that is, as such known, and preferably at a point that is also parallel to the direction in relation to the flow of chips in which gamma-radiating takes place. The measurement signals are synchronized with each other, taking into account the distance between them and the speed of the conveyor. Measurement takes place, for example, by taking the average value at intervals of 1–5 seconds, which improves the measurement statistics. The surface level indicates the thickness of the flow of wood chips, because the surface-level gauge is at a predetermined height above the upper surface of the conveyor carrying the flow of chips.

When using a trough-shaped conveyor, the surface height of the layer of wood chips is preferably measured using ultrasound. No measurement of the surface level of the flow of wood chips is required, however, if the thickness of the blanket of chips on the conveyor is constant. According to one preferred embodiment of the invention, this can be implemented by feeding so many chips onto a trough-shaped conveyor, that the entire surface of the flow of wood chips is at the level of the edges of the conveyor, when the excess chips are removed over the edges of the conveyor, by, for example, using a scraper set at an angle across the conveyor and set against its edges.

Seasonal variations in the volume of air in the wood chips can, according to the invention, be taken into account by measuring the volume of air at regular intervals, and correcting the moisture content of the wood chips calculated on the basis of the continuous measurements, if the volume of air has varied from a set value.

The volume of air in the flow of wood chips can also be stabilized, according to an alternative embodiment of the present invention, by compressing the flow of wood chips before the gamma radiation and the possible measurement of its surface level.

The invention also concerns an arrangement, of the type referred to in the preface, for measuring the moisture content of wood chips, in which there is a transmitter-receiver type ultrasound device above the wood-chip conveyor, for measuring the surface level of the wood chips transported by the conveyor. A detector and the ultrasound device are also connected to a counter, for calculating the moisture content of the wood chips being transported by the conveyor, on the basis of the signals given by the detector and the ultrasound device.

In one embodiment of the invention, there is an endless belt, roller, or similar, for compressing the wood chips transported by the conveyor, set above the conveyor and before the source of gamma radiation and the ultrasound device in the director of travel of the conveyor, to stabilize the volume of air in the wood chips.

The method and arrangement according to the invention can also be used to determine the average moisture content of a log, after first converting the log or a representative sample of it into wood chips.

BRIEF DESCRIPTION OF THE DRAWINGS

In the following, the invention is described in greater detail with reference to the accompanying drawing, which shows a perspective picture of a preferred embodiment of the invention, seen at an angle from above. However, the drawing shows only the elements that are essential for understanding the invention and the length of the conveyor to which these elements relate.

DETAILED DESCRIPTION OF THE INVENTION

In the drawing, the conveyor is marked with the reference number 1. It will be seen that conveyor 1 has a trough-shaped cross-section, i.e. that it has longitudinal edges 3, which rise substantially above its centre. The flow of wood chips that lies on conveyor 1 and travels with it is marked with the reference number 2.

Inside conveyor 1 is an endless belt 9 that is arranged to run around hitch rolls 12 and is set at such a distance from the bottom of the conveyor that it compresses the wood chips travelling on conveyor 1, to stabilize the volume of air in the flow of chips. It is, as such, sufficient, if the levelling and stabilization of the flow of wood chips take place over a quite narrow band, as the measurement beam 7 is only 0,5–1 cm wide while even the ultrasound measurement does not require a great width.

After endless belt 1, in the direction of travel of conveyor 1, a transmitter-receiver type ultrasound device 6 is fitted above conveyor 1 at a predetermined distance of the bottom of conveyor 1, by means of which the surface level of the compressed flow of wood chips 2, and thus the thickness of the blanket of wood chips on the conveyor are measured, as these may vary.

After ultrasound device 6 in the direction of travel of conveyor 1, a gamma radiation source 4 is also fitted above conveyor 1, as well as an upper collimator 10, for creating collimated gamma radiation 7. At a corresponding point on the conveyor, but beneath it, there are a lower collimator 11 and a corresponding detector 5, which are used to measure the proportion of gamma radiation that has passed through the compressed flow of wood chips 2, of the amount of gamma radiation directed onto it. Thus, the gamma radiation transmitter 4 and the corresponding detector 5, i.e. the receiver, lie on the same vertical line on opposite sides of conveyor 1.

The signals obtained from detector 5 and ultrasound source 6 are led to a counter 8, the signal obtained from which expresses the moisture content of the flow of wood chips 2. Counter 8 also takes into account the total amount of gamma radiation transmitted by gamma radiation source 4 and the amount of air in the flow of wood chips 2, which is measured separately at regular intervals. As the amount of air in the wood chips varies from conveyor to conveyor, the system must be calibrated for each conveyor.

It is obvious that the invention can be varied extensively within the scope defined by the accompanying Claims.

Thus, for example, the straight line running through the gamma radiation source and the detector need not be directly vertical, but may form an acute angle with the horizontal, and may even actually be horizontal, in which case the gamma radiation source and detector will lie on the same horizontal level, on opposite sides of the conveyor. So many wood chips are then fed to the conveyor that the level of the flow of wood chips remains higher than the horizontal level of the gamma radiation source and the detector, so that the gamma radiation always travels through an equally thick layer of wood chips. In that case, there is no need to measure the height of the layer of wood chips, as the length of a ray is known from the geometry of the conveyor. Though in the drawing the gamma radiation source is above the conveyor and the detector is beneath it, the opposite arrangement may also be used. A scintillation detector or proportional counter, which can measure a source of radio isotopes, can be used as the detector.

Instead of an ultrasound device, the surface level of the layer of wood chips can be measured using some other device, for example, a broad roller that moves mechanically to follow the surface of the flow of wood chips. The surface level measuring device can equally well be after the gamma radiation source/detector in the direction of travel of the conveyor. In this case too, the counter allows for the distance between the surface level measuring device and the gamma radiation source/detector, the speed of the conveyor, and the order in which they are in the direction of travel of the conveyor.

The cross-sectional shape of the conveyor need not be curved, but may be any other shape as well, along as the side edges are essentially higher than its central part, so that the height of the surface of the flow of wood chips and its cross-sectional shape cannot change between the levelling of the surface or measurement of the surface and the measurement of the transmission of the gamma radiation.

The flow of wood chips can be compressed to stabilize its air content in other ways than by using an endless belt, for example, by using a broad roller that rotates freely on top of the flow of wood chips, and which has a predetermined weight.

The aforesaid proportional value of the total mass can also be expressed as the result of the average density and layer thickness.

Although the invention has been described by reference to specific embodiments, it should be understood that numerous changes may be made within the spirit and scope of the inventive concepts described. Accordingly, it is intended that the invention not be limited to the described embodiments, but that it have the full scope defined by the language of the following claims.

What is claimed is:

1. A method for measuring the moisture content of wood chips by forming an essentially homogenous flow of wood chips, directing gamma radiation essentially transversely through the flow of wood chips, measuring the attenuation of the gamma radiation passing through the flow of wood chips, and by determining the proportional value of the total mass at the penetration point of the gamma radiation, in which case, the moisture content is obtained as a function of this value and the measured attenuation, characterized in that the gamma radiation is collimated from at least one side of the flow of wood chips, to create a measurement ray, the length of this measurement ray in the flow of wood chips is measured, and the air content of the flow of wood chips is determined, in which case the proportional value of the aforesaid mass is determined with the aid of the aforesaid length and air content.

2. A method according to claim 1, characterized in that the flow of wood chips is shaped by transporting it on a conveyor with a trough-shaped cross-section, the gamma radiation being directed essentially vertically through the flow of wood chips and the conveyor, and measuring the surface level of the flow of wood chips on the trough-shaped conveyor at a point, which is preferably essentially on the same straight line in the direction of travel of the wood chips as the gamma radiation.

3. A method according to claim 2, characterized in that the surface level of the flow of wood chips on the trough-shaped conveyor is measured using ultrasound.

4. A method according to claim 1, characterized in that the wood chips are fed onto the conveyor with a trough-shaped cross-section up to its edges, the part that is higher than the edges being levelled to the height of the edges and the excess being removed over the edges, and the gamma radiation being directed essentially vertically through the levelled flow of wood chips and the conveyor.

5. A method according to claim 1, characterized in that the air content of the wood chips is measured at regular intervals and the measurement result obtained is used to correct the moisture content of the wood chips calculated on the basis of the continuous measurement results.

6. A method according to claim 1, characterized in that the flow of wood chips is compressed before the gamma radiation, to stabilize the air content.

7. An arrangement to measure the moisture content of wood chips, comprising a wood-chip conveyor with raised sides forming a flow of wood chips and on opposite sides of it a source of gamma radiation and a corresponding detector arranged to essentially overlap, characterized by at least one collimator for forming a collimated measurement ray and an ultrasound device above the wood-chip conveyor for measuring the surface level of the wood chips transported on the conveyor, and a device for measuring the moisture content of the wood chips transported on the conveyor on the basis of the measurement signals provided by the detector and the ultrasound device and the predetermined amount of air in the flow.

8. An arrangement according to claim 7, characterized in that the wood-chip conveyor has a trough-shaped cross-section.

9. An arrangement according to claim 7, characterized by a compression device above the wood-chip conveyor seen in its direction of travel before the source of collimated gamma radiation and the ultrasound device, for compressing the wood chips transported by the conveyor, to stabilize their air content.

10. An arrangement according to claim 9, characterized in that the compression device is one of a roller, endless belt, or similar.

* * * * *